United States Patent
Berlinger et al.

(10) Patent No.: US 11,511,131 B2
(45) Date of Patent: Nov. 29, 2022

(54) RADIATION TREATMENT PARAMETERS FOR TARGET REGION TUMOUR

(71) Applicant: Brainlab AG, Munich (DE)

(72) Inventors: Kajetan Berlinger, Munich (DE); Michael Stead, Unterhaching (DE)

(73) Assignee: Brainlab AG, Munich (DE)

( * ) Notice: Subject to any disclaimer, the term of this patent is extended or adjusted under 35 U.S.C. 154(b) by 402 days.

(21) Appl. No.: 16/537,886

(22) Filed: Aug. 12, 2019

(65) Prior Publication Data

US 2021/0046328 A1 Feb. 18, 2021

(51) Int. Cl.
*A61N 5/10* (2006.01)

(52) U.S. Cl.
CPC ......... *A61N 5/1049* (2013.01); *A61N 5/1068* (2013.01); *A61N 2005/105* (2013.01); *A61N 2005/1051* (2013.01); *A61N 2005/1055* (2013.01); *A61N 2005/1059* (2013.01); *A61N 2005/1061* (2013.01); *A61N 2005/1087* (2013.01)

(58) Field of Classification Search
CPC .......... A61N 2005/1087; A61N 5/1049; A61N 2005/105; A61N 2005/1055; A61N 2005/1059; A61N 2005/1051; A61N 2005/1061; A61N 5/1068
See application file for complete search history.

(56) References Cited

U.S. PATENT DOCUMENTS

| | | | | |
|---|---|---|---|---|
| 8,597,211 B2 * | 12/2013 | Berlinger | ................ | G06T 7/248 600/595 |
| 2018/0185671 A1 * | 7/2018 | Filiberti | ............... | A61N 5/1069 |

FOREIGN PATENT DOCUMENTS

| | | |
|---|---|---|
| WO | 2017140352 A1 | 8/2017 |
| WO | 2018219432 A1 | 12/2018 |

OTHER PUBLICATIONS

Ehrbar et al. "ITV, mid-ventilation, gating or couch tracking—A comparison of respiratory motion-management techniques based on 4D dose calculations", Radiotherapy Oncology, Jul. 2017, vol. 124, issue 1, pp. 80-88.

* cited by examiner

*Primary Examiner* — Christine H Matthews
*Assistant Examiner* — Joshua Daryl D Lannu
(74) *Attorney, Agent, or Firm* — Middleton Reutlinger

(57) ABSTRACT

Disclosed is a computer-implemented method which encompasses comparing the requirements for radiation therapy imposed by a patient's individual condition to the capabilities and requirements of different types of treatment machines to determine a suitable radiation treatment strategy including an identification of the treatment machine which shall be used and a treatment plan. Furthermore, a treatment plan is generated by simulating the envisaged radiation treatment. The type of treatment machine associated with a predetermined value for the sum of weights for all fields assigned to that treatment machine is determined as the treatment machine for treating the patient, and corresponding information is output detailing the treatment specifics such as radiation treatment parameters specifically suited for the patient target region tumor thereby reducing radiation exposure, efficient use of the machine and appropriate gating and tracking modes.

13 Claims, 4 Drawing Sheets

RADIATION TREATMENT PARAMETERS FOR TARGET REGION TUMOUR

FIELD OF THE INVENTION

The present invention relates to a computer-implemented method of determining a radiation treatment procedure for radiation treatment of a target region subject to vital movement, a corresponding computer program, a program storage medium storing such a program and a computer for executing the program, as well as a medical system comprising an electronic data storage device and the aforementioned computer.

TECHNICAL BACKGROUND

There are many different strategies how to treat a patient using radiotherapy, especially when it comes to motion management considering a target region which is subject to a vital movement such as breathing motion or heartbeat. Especially targets that move due to respiration pose a challenge to medical staff.

Most lung tumours for instance are treated using the internal target volume (ITV) approach, but depending on the movement of the tumour, more sophisticated techniques like gating or tracking are taken into account. This in turn requires certain treatment hardware. Many hospitals have different types of linear accelerators, each linear accelerator being specialized for use with certain indications.

Treatment time is also an important issue. Gating for instance is a time-consuming process. It strictly depends on the compliance demonstrated by the patient.

Furthermore, at the point in time of planning so far, the user does not know whether the target region will be e.g. trackable via kV imaging (projection radiographies). The question has to be answered whether it is necessary to track an indicator, and if so which indicator, or whether an implanted marker is necessary. All these things shall be simulated for instance using physically correct DRR (digitally rendered radiograph) sequences created from a four-dimensional computed tomography.

The present invention has the object of providing an improved method of determining a radiation treatment procedure and radiation treatment control parameters.

The present invention can be used for planning procedures e.g. in connection with a system for image-guided radiotherapy such as VERO® and ExacTrac®, and "Elements" radiotherapy planning software, all products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses comparing the requirements for radiation therapy imposed by a patient's individual condition to the capabilities and requirements of different types of treatment machines to determine a suitable radiation treatment strategy and control radiation control parameters including an identification of the treatment machine which shall be used and a treatment plan. This involves using a look-up table defining the requirement imposed by the patient's condition and a look-up table defining the capabilities of each type of treatment machine, and weighting the fields of the look-up table defining the requirement imposed by the patient's condition depending on whether they fit to the corresponding field the look-up table defining the capabilities of each type of treatment machine. Furthermore, a treatment plan is generated by simulating the envisaged radiation treatment. The type of treatment machine associated with a predetermined value for the sum of weights for all fields assigned to that treatment machine is then selected as the treatment machine for treating the patient, and corresponding information is output, e.g. visually, to a user along with the treatment plan including radiation treatment control parameters to appropriately treat the patient with identified condition.

General Description of the Invention

In this section, a description of the general features of the present invention is given for example by referring to possible embodiments of the invention.

In general, the invention reaches the aforementioned object by providing, in a first aspect, a computer-implemented medical method of determining a radiation treatment procedure for radiation treatment of a target region subject to vital movement (such as breathing motion or heartbeat). The method comprises executing, on at least one processor of at least one computer (for example at least one computer being part of a navigation system), the following exemplary steps which are executed by the at least one processor.

In a (for example first) exemplary step, medical patient image data is acquired which describes a time-dependent series of digital patient images of the target region, wherein the target region is included in an anatomical body part of a patient. The digital patient images have been generated for example by applying a tomographic imaging modality such as magnetic resonance imaging or computed x-ray tomography or ultrasound tomography, or a non-tomographic imaging modality such as radiography to the anatomical body part and specifically the target region.

In a (for example second) exemplary step, amplitude data is acquired based on the medical patient image data. The amplitude data describes an amplitude of the vital movement of the target region, for example the amplitude is the conventional amplitude, or for example the amplitude is the peak-to-peak amplitude.

In a (for example third) exemplary step, availability data is acquired which describes the availability of breathing curve data describing an external breathing curve of the patient. The breathing curve data has for example been generated by detecting a breathing motion of the patient's thorax by tracking, using a for example an infrared camera-based tracking system, retroreflective optical markers attached to the thorax or by surface scanning, using for example a laser scanner, of the thorax during breathing motion.

In a (for example fourth) exemplary step, treatment machine capability data is acquired which describes the imaging and beam control capabilities as well as the achievable dose rate of a plurality of radiation treatment machines.

In a (for example fifth) exemplary step, machine control data is acquired which describes a treatment time associated with a size of the target region and different modes of imaging and beam activation by different types of treatment machines for conducting radiation treatment and conditions for the amplitude of the vital movement, availability of an external breathing curve associated with the size of the target region and the different modes of imaging and beam activation by the different types of treatment machines for conducting radiation treatment. For example, the modes of imaging describe points in time at which the target region shall be imaged during execution of the radiation treatment.

For example, the modes of beam activation include a gating mode and a tracking mode, wherein the gating mode includes a modulation of a geometry of a treatment beam to be emitted by the treatment machine and the tracking mode includes tracking a position of the target region with the treatment beam. For example, the size of the target region is defined by the internal target volume.

In a (for example sixth) exemplary step, weight data is determined which describes an individual patient-dependent weight for the information contained in the machine control data, wherein an individual weight is assigned to each set of information. The weight data is determined based on the amplitude data and the availability data and the machine control data. For example, the weights are added for each type of treatment machine, and wherein the type of treatment machine associated with the highest sum of weights is selected as the type of treatment machine to be used for treating the target region. For example, at least one of the weights is set to a predetermined value, for example zero, if the set of information with which it is associated is not applicable to the patient. For example, if it is determined that a machine type associated with the set of information for which the weight is set to the predetermined value, this machine type is not selected as the type of treatment machine to be used for treating the target region.

In a (for example seventh) exemplary step, machine type data is determined which describes a type of treatment machine to be used for treating the target region. The machine type is determined based on the amplitude data and the availability data and the treatment time data and the machine control data and the weight data and the treatment time data and the treatment machine capability data. For example, this involves comparing the conditions for the amplitude of the vital movement, availability of an external breathing curve, and the treatment time associated with different modes of beam activation control described by the machine control data to the respective information described by the amplitude data, availability data and treatment time data, respectively, and assigning the weights according to the result of the comparison.

In a (for example eighth) exemplary step, treatment procedure data is determined which describes a radiation treatment to be applied to the target region using the type of treatment machine described by the machine type data. The treatment procedure data is determined based on the machine type data.

In a further exemplary step of the method according to the first aspect, the radiation treatment is simulated using the machine parameters of the type of treatment machine described by the machine type data.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a computer-readable program storage medium on which the program according to the second aspect is stored. The program storage medium is for example non-transitory.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:

a) the at least one computer according to the fourth aspect;

b) at least one electronic data storage device storing at least the medical patient image data and the treatment plan data and the availability data and the treatment time data and the treatment machine capability data and the machine control data, wherein the at least one computer is operably coupled to the at least one electronic data storage device for acquiring, from the at least one data storage device, at least the medical patient image data and the treatment plan data and the availability data and the treatment time data and the treatment machine capability data and the machine control data, and the at least one electronic data storage device for storing, in the at least one data storage device, at least the treatment procedure data.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of executing the determined radiation treatment procedure. More particularly, the invention does not involve or in particular comprise or encompass any surgical or therapeutic activity. The invention is instead directed as applicable to the field of computing such a radiation treatment procedure. For this reason alone, no surgical or therapeutic activity and in particular no surgical or therapeutic step is necessitated or implied by carrying out the invention.

The present invention also relates to the use of the device/system or any embodiment thereof for planning a radiation treatment procedure. The use comprises for example at least one the steps of the method according to the first aspect.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, Ill-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the World Wide Web (WWW) and located in a so-called cloud of computers which are all connected to the World Wide Web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (World Wide Web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data.

Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

Movements of treatment body parts such as the target of radiation treatment may for example be due to movements which are referred to in the following as "vital movements". Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. For example, analytical devices are constituted to perform medical imaging methods. Analytical devices for example use medical imaging methods and are for example devices for analyzing a patient's body, for instance by using waves and/or radiation and/or energy beams, for example electromagnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analyzing the body. Analytical devices are for example used in medical diagnosis, for example in radiology. However, it can be difficult to identify the treatment body part within the analytical image. It can for example be easier to identify an indicator body part which correlates with changes in the position of the treatment body part and for example the movement of the treatment body part. Tracking an indicator body part thus allows a movement of the treatment body part to be tracked on the basis of a known correlation between the changes in the position (for example the movements) of the indicator body part and the changes in the position (for example the movements) of the treatment body part. As an alternative to or in addition to tracking indicator body parts, marker devices (which can be used as an indicator and thus referred to as "marker indicators") can be tracked using marker detection devices. The position of the marker indicators has a known (predetermined) correlation with (for example, a fixed relative position relative to) the position of indicator structures (such as the thoracic wall, for example true ribs or false ribs, or the diaphragm or intestinal walls, etc.) which for example change their position due to vital movements.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionizing radiation is for example used for the purpose of treatment. For example, the treatment beam comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionizing radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimization algorithms are applied in order to find the transformation which results in an optimum degree of similarity. The degree of similarity is preferably measured by way of a measure of similarity (also referred to in the following as a "similarity measure"). The parameters of the optimization algorithm are for example vectors of a deformation field. These vectors are determined by the optimization algorithm in such a way as to result in an optimum degree of similarity. Thus, the optimum degree of similarity represents a condition, for example a constraint, for the optimization algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimizing problem is for example solved iteratively, for example by means of an optimization algorithm which is for example a first-order optimization algorithm, such as a gradient descent algorithm. Other examples of optimization algorithms include optimization algorithms which do not use derivations, such as the downhill simplex algorithm, or algorithms which use higher-order derivatives such as Newton-like algorithms. The optimization algorithm preferably performs a local optimization. If there is a plurality of local optima, global algorithms such as simulated annealing or generic algorithms can be used. In the case of linear optimization problems, the simplex method can for instance be used.

In the steps of the optimization algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighboring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A navigation system, such as a navigation system for image-guided radiotherapy, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
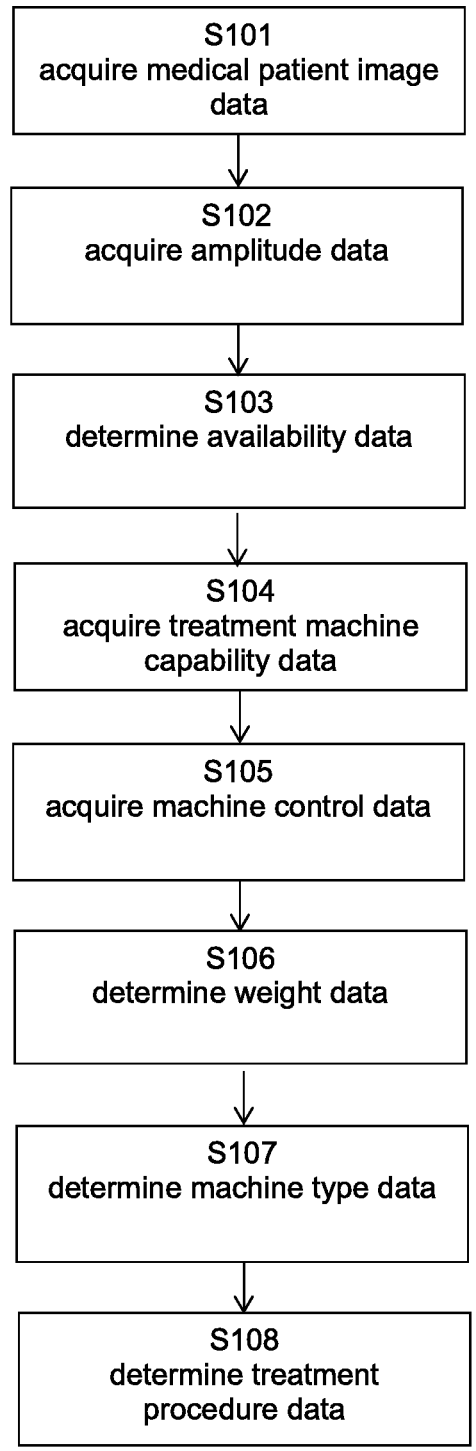
FIG. 1 illustrates a basic flow of the method according to the first aspect.

FIG. 1 illustrates the basic steps of the method according to the first aspect, in which step S101 encompasses acquisition of the medical patient image data, step S102 encompasses acquisition of the amplitude data, and subsequent step S103 encompasses determination of the availability data. Then, the treatment machine capability data and the machine control data are acquired in steps S104 and S105, respectively, followed by determination of the weight data in step S106. On the basis of the foregoing data processing, the machine type data is determined in step S107, and then the treatment procedure data is determined instep S108. Treatment procedure data can include radiation treatment parameters to be applied to the target region using the type of treatment machine of the treatment machine type and may include the applicable motion management strategy, patient position for imaging by, for example, a cone-beam computed tomography device or a radiography device, how to generate the breathing curve, how to localize/track the target region, the desired monitoring behavior while the beam is emitted and other radiation treatment specifics. Such data can also include modes of beam activation including gating mode data and tracking mode data.

Figure 2:
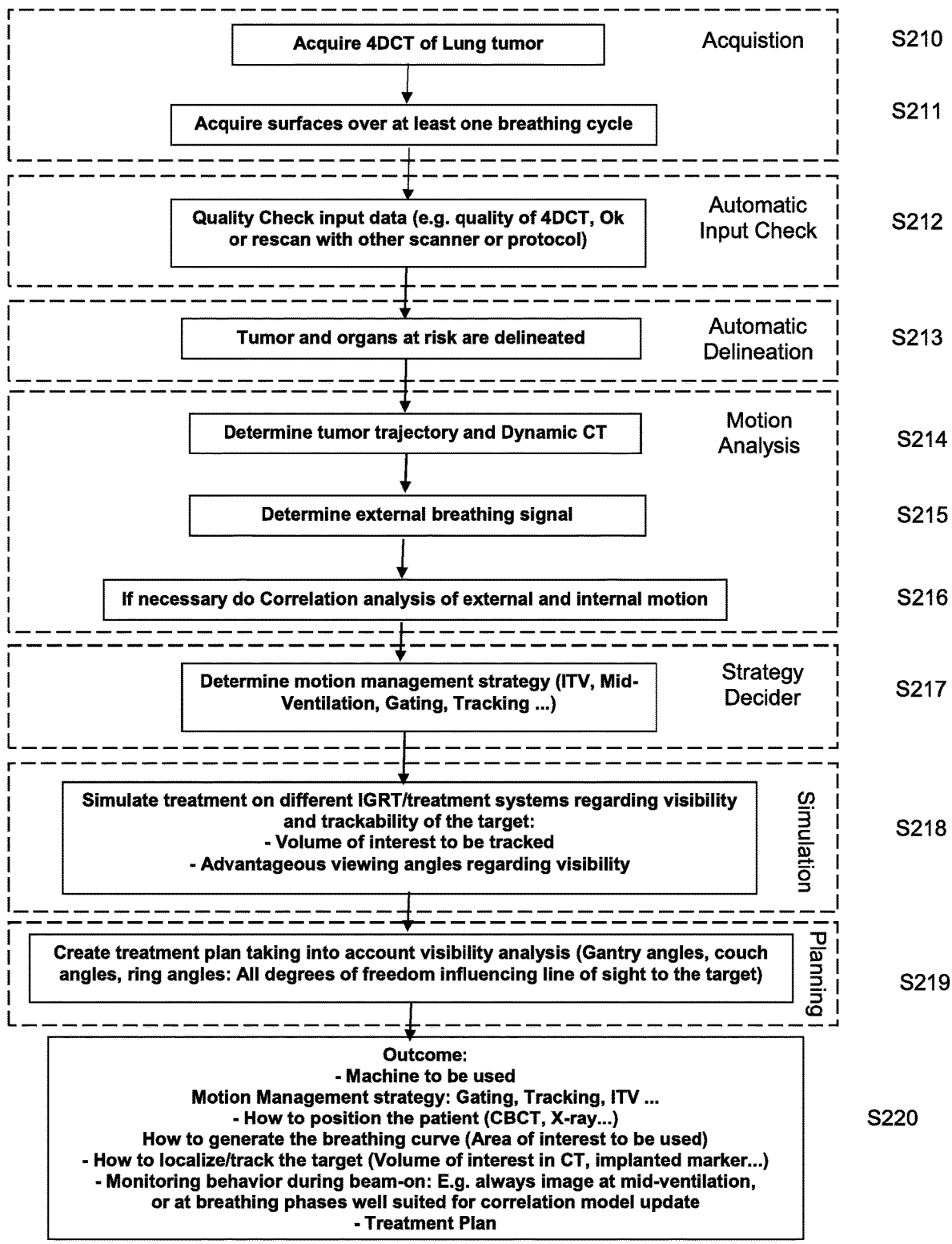
FIG. 2 shows an embodiment of the method according to the first aspect.

FIG. 2 describes an example embodiment of the method illustrated in FIG. 1: in step S210, the medical patient image data is acquired as a 4D-CT (four-dimensional computed x-ray tomography, i.e. a computed x-ray tomography which has a time component), and the target region is embodied by a lung tumour. Then, the breathing curve data is acquired in step S211 by surface scanning of the thorax over at least one breathing cycle. This is followed by an automatic input check which involves, in step S212, quality check of the input data for determining e.g. the quality of the 4D-CT to determine a need for re-scanning the anatomical body part with another scanner or scanning protocol of the quality check results in that the 4D-CT is not ok. Then, an automatic delineation of the tumour and organs at risk is conducted in step S213, for example by acquiring atlas data describing an image-based model of the anatomical body part and a definition of anatomical regions such as organs at risk. The atlas data is then matched with the medical patient image data, for example by applying a fusion algorithm to both data sets. The result of the fusion allows delineation and/or segmentation of the corresponding anatomical regions (such as organs at risk) in the digital patient images. The position of the target region may be determined by finding deviations between the digital patient images and the image-based model, for example by assuming that the tumour is a structure which is not present in the image-based model. A motion analysis is then conducted by determining a trajectory of the tumour and a dynamic computed x-ray tomography (CT) in step S214, an external breathing signal (external breathing curve) in step S215, and, if necessary, by performing a correlation analysis of external and internal motion of the anatomical body part in step S216. In step S217, the strategy decider module is executed for determining the applicable motion management strategy such as the internal target volume approach, mid-ventilation irradiation, gating, or target tracking. Then, the radiation treatment is simulated in step S218. The simulation is done for different image-guided radiotherapy (IGRT) treatment systems regarding visibility and trackability of the target for the imager in consideration of the volume of interest to be tracked and advantageous viewing angles for generation the desired visibility. Then, the planning takes place by creating, in step S219, a treatment plan taking into account the visibility angles (such as gantry angles, couch angles, ring angles—each time considering all degrees of freedom influencing the line of sight to the target region). In step S220, the output of the method is generated by identifying the treatment machine to be used, the applicable motion management strategy, how to position the patient for imaging by for example a cone-beam computed tomography device (CBCT) or a radiography device (x-ray machine), how to generate the breathing curve (specifically, the area of interest on the patient's body to be used as a reference), how to localize/track the target region (e.g. by defining a volume of interest in the CT image which shall be tracked or the position of an implanted marker in the CT image which shall be tracked), the desired monitoring behavior while the beam is emitted (during beam-on), e.g. whether monitoring (imaging) is to be conducted always at mid-ventilation or a breathing phases well-suited for updating a correlation model. This treatment procedure data may be output to an operator for later entry into a treatment machine, transferred to a treatment machine and/or provided for treatment radiation mode and control and/or may be utilized to control the positioning of the patient during the treatment procedure. The output may be transferred to the treatment machine by operator, electronically, wirelessly or be determined and fully integrated therewith. Additionally, the output comprises a treatment plan for radiation treatment of the target region.

Figure 3:
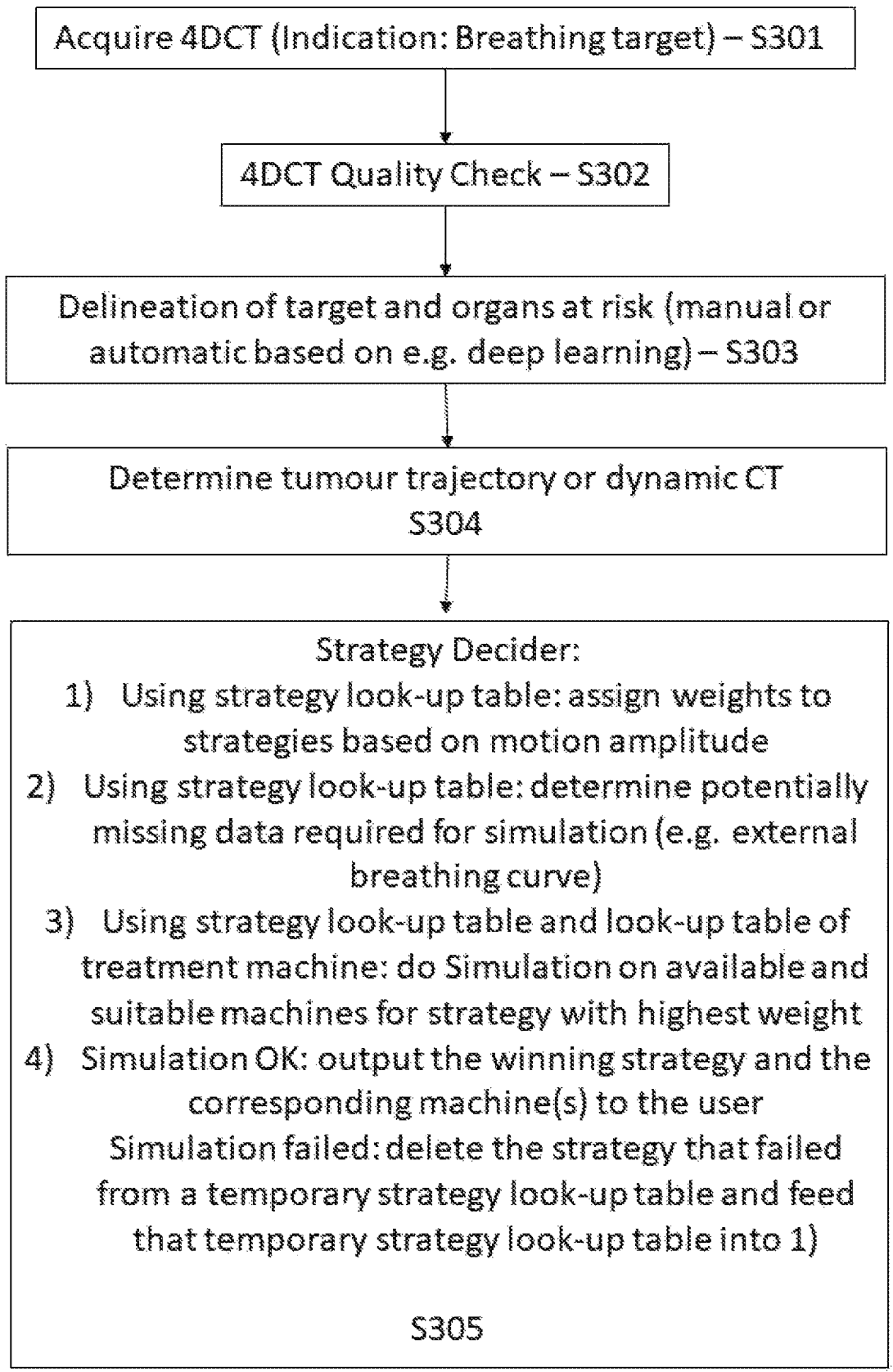
FIG. 3 shows details of a strategy decider module for determining the radiation treatment procedure.

FIG. 3 shows details of the strategy decider module and its use in an example of the method according to the first aspect. Steps S301 to S304 correspond to steps S210, S212, S213 and S214, respectively, of FIG. 2. In step 305, the strategy decider module is executed. This involves using a strategy look-up table such as the one shown in Table 1. This table assigns weights to strategies (i.e. radiation treatment procedures), i.e. to every field of the strategy look-up table) based on the motion amplitude of the vital movement of the target structure, as illustrated by Table 3. If the signal does not correlate with the trajectory, then no prediction based, e.g. Gating or Tracking based strategies are possible (exit criterion). Also using the strategy look-up table, potentially missing data which is required for a simulation (e.g. an external breathing curve) is determined. Using the strategy Look-up table and a look-up table of each machine (embodying the treatment machine capability data) such as the one shown in Table 2, a simulation on available and suitable treatment machines is executed for the strategy with the highest weight or sum of weights. If the simulation is ok, an identification of the most effective strategy and the corresponding treatment machine or treatment machines are output to the user. For example, the most effective strategy may be determined by the system after the simulation outlined herein. Not only may acquired or input data be verified to prevent possible improper determination of treatment parameters, but techniques may be determined for tumor motion tracking, patient positioning, tumor localization, and as well, determined breathing curves through motion analysis can be accomplished. These determinations result in more accurate, less time consuming and more direct treatment of the tumor by the most appropriate machine, technique and method. This includes such gating and tracking data as well as relative patient position data for proper positioning of the treatment area relative to the radiation source. If the simulation fails, the strategy that failed is deleted from a temporary strategy look-up table, and the temporary strategy look-up table is then fed into sub-step 1) of step S305.

TABLE 1

Strategy Lookup-Table (Lung): (Manually filled by experts, or automatically retrieved from cloud/big data/journals/publications . . . )

| | ITV | Midventilation | Gating | Tracking |
|---|---|---|---|---|
| Essential data for indication | 4DCT | | | |
| Target motion amplitude | <8 mm | >=8 mm <=15 mm | >15 mm | >15 mm |
| Additional Data required (for simulation) | — | — | external breathing curve | external breathing curve |
| PTV Margins for Treatment Planning | Moderate | Tight | Very Tight | Very Tight |

TABLE 1-continued

Strategy Lookup-Table (Lung): (Manually filled by experts, or automatically retrieved from cloud/big data/journals/publications . . . )

|  | ITV | Midventilation | Gating | Tracking |
|---|---|---|---|---|
| Required simulation | — | — | Target Trackability and Correlation Analysis (ext. Int. Motion) | Target Trackability and Correlation Analysis (ext. Int. Motion) |
| Treatment Time | 10 min | 10 min | 20 min | 15 min |
| Required HW for Treatment | CBCT | CBCT | Gating Support | Tracking Support |

TABLE 2

(Available) Machines' Lookup-Table: (Manually filled, or automatically retrieved from internet)

|  | TrueBeam with ETX | Cyberknife | Vero | ExacTrac |
|---|---|---|---|---|
| CBCT | YES | NO | YES | No |
| Gating | No | No | No | Yes |
| Tracking | No | Yes | Yes | No |
| Implanted Marker Support | No | Yes | Yes | No |
| Stereo X-ray | No | Yes | Yes | Yes |
| X-ray imager not fixed (higher probability that target is visible) | Yes | No | Yes | No |
| Dose Rate (the higher the shorter the treatment time) | 2000 | 1000 | 1000 | — |

TABLE 3

| Weights through Simulation | Gating on System A | Tracking on System B |
|---|---|---|
| Does external respiratory signal correlate with internal target trajectory? | Yes: 1 No: 0 (exit criterion) | |
| Are implanted markers needed for internal target tracking? | Yes: 1 No: 3 | Yes: 1 No: 3 |
| Treatment time: | 1 (significantly longer!) | 3 |

Figure 4:
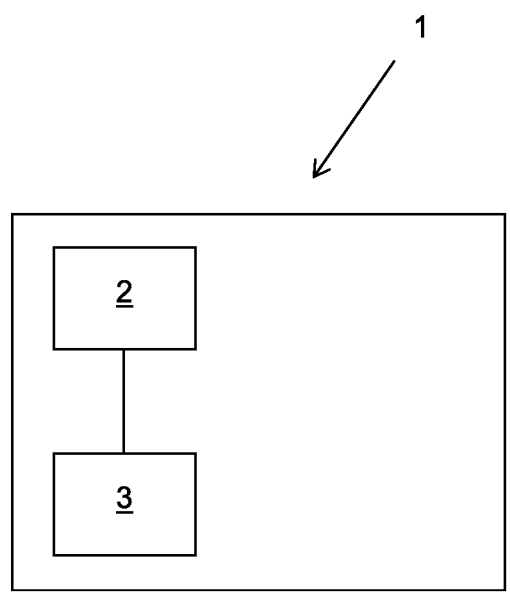
FIG. 4 is a schematic illustration of the system according to the fifth aspect.

FIG. 4 is a schematic illustration of the medical system 1 according to the fifth aspect. The system is in its entirety identified by reference sign 1 and comprises a computer 2, an electronic data storage device (such as a hard disc) 3 for storing at least the medical patient image data and the treatment plan data and the availability data and the treatment time data and the treatment machine capability data and the machine control data. The components of the medical system 1 have the functionalities and properties explained above with regard to the fifth aspect of this disclosure.

The present disclosure relates to a software tool that suggests a complete strategy how to treat a certain patient with radiation therapy, including
  quality check of input data (maybe 4DCT data shows artefacts, then a re-scan should be done)
  delineation of a tumour (automatically (deep learning approaches), or manually)
  motion compensation technique (gating, tracking . . . )
  hardware/treatment machine
  patient positioning (CBCT, kV imaging, EPID)
  monitoring behavior (surface camera with suggested area of interest; kV trigger behavior)
  tumour localization (Will target be visible in radiographies?, Are implanted markers required?, trustworthy indicators)

As input, the software receives a time series of images (4DCT, or FB CT and DIBH CT). Furthermore, as additional input breathing curve data should be taken into account. Via motion analysis and treatment simulation, a complete treatment strategy shall be suggested to the user—the user maybe the physician, physicist or even the patient.

In the following, a short overview of the typical motion management strategies for tumours that move with respiration (cf. Ehrbar et al., ITV, mid-ventilation, gating or couch tracking—A comparison of respiratory motion-management techniques based on 4D dose calculations, Radiotherapy Oncology, July 2017, 124(1):80-88, doi: 10.1016/j.radonc.2017.05.016):

ITV (internal target volume) approach:
Based on the 4DCT the complete area where the target has been located is taken as target volume. Patient is treated in free breathing.

Mid-ventilation approach:
Significantly reduced target volume compared to ITV. The idea is to treat the patient in free-breathing, but concentrate the target volume on the area on the time-averaged mean position, determined from the 4D-CT.

Gating (e.g. at exhale):
The target volume is defined for a specific breathing phase (e.g. exhalation). During treatment, a breathing curve is generated using a specific signaling device (e.g. infrared camera tracking markers on the chest, or a surface camera), and only when the specific breathing phase is reached the treatment beam is turned on, otherwise the beam is off.

Tracking:
The position of the target region is tracked or predicted, and the treatment system takes care that the target region stays in the focus of the radiation beam. There are different approaches: a robotic arm or a gimbal that moves the beam source with the target motion.

MLC tracking: the leafs of the collimator are moved with the motion of target region.

Couch tracking: the couch (and thereby the patient) is moved with the motion of target region.

Deep-Inspiration Breath-Hold (DIBH):
Mostly used when treating left-sided breast cancer. The heart is sensitive to radiation. The heart is located close to the left breast. With inhalation the heart is moved caudally by the diaphragm, and the chest moves the breast in anterior direction. Thus, the heart is moved out of the radiation beam.

Utilization of the systems and methods described herein result in more efficient use of the treatment machines, for example, to treat patient tumors. For example, in some implementations, the determined treatment procedure data output may include radiation treatment parameters specifically suited for the patient target region thereby reducing radiation exposure, efficient use of the machine and appropriate gating and tracking modes, wherein the gating mode includes a modulation of a geometry of a treatment beam to be emitted by the treatment machine and the tracking mode includes tracking a position of the target region with the treatment beam. Other parameters may be determined in the machine type data and the determined treatment procedure data to ensure efficient utilization of the treatment machine, reduction in necessary energy utilized by the treatment machine and formulated exposure of the treatment beam to thereby focalize treatment beam exposure to the treatment site and reduce exposure to non-treatment locations.

The invention claimed is:

1. A computer-implemented method of determining a radiation treatment procedure for radiation treatment of a target region subject to vital movement, comprising:
   acquiring medical patient image data describing a time-dependent series of digital patient images of the target region, wherein the target region is included in an anatomical body part of a patient;
   determining, based on the medical patient image data, amplitude data describing an amplitude of the vital movement of the target region;
   acquiring availability data describing an availability of breathing curve data describing an external breathing curve of the patient;
   acquiring treatment machine capability data describing imaging and beam control capabilities as well as an achievable dose rate of a plurality of radiation treatment machines;
   acquiring machine control data describing a treatment time associated with a size of the target region and a respective mode of different modes of imaging and beam activation by different types of treatment machines contained in the plurality of radiation treatment machines for conducting the radiation treatment and conditions for the amplitude of the vital movement, and availability of an external breathing curve associated with the size of the target region and the respective mode of the different modes of imaging and beam activation by the different types of treatment machines for conducting the radiation treatment;
   determining, based on the amplitude data and the availability data and the machine control data, weight data describing individual patient-dependent weights for information contained in the machine control data and divided into a plurality of sets, wherein an individual weight is assigned to each set, of the plurality of sets, of the information;
   determining, based on the amplitude data and the availability data and the machine control data and the weight data and the treatment machine capability data, machine type data describing a type of treatment machine, from the different types of treatment machines, to be used for treating the target region;
   determining, based on the machine type data, treatment procedure data describing the radiation treatment to be applied to the target region using the type of treatment machine described by the machine type data;
   selecting, based on the determined type of treatment machine and the treatment procedure data, a treatment machine out of the plurality of radiation treatment machines to treat the target region; and
   outputting the treatment procedure data to the selected treatment machine to control radiation treatment parameters to reduce radiation exposure.

2. The method according to claim 1, wherein the individual patient-dependent weights are added for each type of treatment machine, and wherein the type of treatment machine associated with a highest sum of the individual patient-dependent weights is selected as the type of treatment machine to be used for treating the target region.

3. The method according to claim 1, wherein at least one of the individual patient-dependent weights is set to a predetermined value, upon determining that a set of information with which the at least one of the individual patient-dependent weights is associated is not applicable to the patient.

4. The method according to claim 3, wherein, upon determining that a particular machine type is associated with the set of information for which the at least one of the individual patient-dependent weight is set to the predetermined value, the particular machine type is not selected as the type of treatment machine to be used for treating the target region.

5. The method according to claim 1, wherein
   the conditions for the amplitude of the vital movement, the availability of the external breathing curve, and the treatment time associated with the different modes of beam activation described by the machine control data, are compared to respective information described by the amplitude data, availability data and treatment time data, respectively, and
   the individual patient-dependent weights are assigned according to a result of comparison.

6. The method according to claim 1, further comprising simulating the radiation treatment using machine parameters of the type of treatment machine described by the machine type data.

7. The method according to claim 1, wherein the different modes of imaging describe points in time at which the target region shall be imaged during execution of the radiation treatment.

8. The method according to claim 1, wherein the different modes of beam activation include a gating mode and a tracking mode, wherein the gating mode includes a modulation of a geometry of a treatment beam to be emitted by the determined type of treatment machine and the tracking mode includes tracking a position of the target region with the treatment beam.

9. The method according to claim 1, wherein the size of the target region is defined by an internal target volume.

10. The method of claim 1 further comprising providing the determined treatment procedure data describing the radiation treatment to be applied, wherein the providing causes operation of the determined type of treatment machine to operate based on the determined treatment procedure data for treating the target region.

11. A non-transitory computer-readable program storage medium storing a program which, when running on at least one processor of at least one computer, causes the at least one processor to:
   acquire medical patient image data describing a time-dependent series of digital patient images of a target region, wherein the target region is included in an anatomical body part of a patient;
   determine, based on the medical patient image data, amplitude data describing an amplitude of a vital movement of the target region;

acquire availability data describing an availability of breathing curve data describing an external breathing curve of the patient;

acquire treatment machine capability data describing imaging and beam control capabilities as well as an achievable dose rate of a plurality of radiation treatment machines;

acquire machine control data including treatment time data describing a treatment time associated with a size of the target region and a respective mode of different modes of imaging and beam activation by different types of treatment machines contained in the plurality of radiation treatment machines for conducting a radiation treatment and conditions for the amplitude of the vital movement, and availability of an external breathing curve associated with the size of the target region and the respective mode of the different modes of imaging and beam activation by the different types of treatment machines for conducting the radiation treatment;

determine, based on the amplitude data and the availability data and the treatment time data and the machine control data, weight data describing individual patient-dependent weights for information contained in the machine control data and divided into a plurality of sets, wherein an individual weight is assigned to each set, of the plurality of sets, of the information;

determine, based on the amplitude data and the availability data and the weight data and the treatment machine capability data, machine type data describing a type of treatment machine, from the different types of treatment machines, to be used for treating the target region;

determine, based on the machine type data, treatment procedure data describing the radiation treatment to be applied to the target region using the type of treatment machine described by the machine type data;

select, based on the determined type of treatment machine and the treatment procedure data, a treatment machine out of the plurality of radiation treatment machines to treat the target region; and output the treatment procedure data to the selected treatment machine to control radiation treatment parameters to reduce radiation exposure.

12. At least one computer comprising at least one processor and associated memory, the memory having instructions stored thereon which when executed cause the at least one processor to:

acquire medical patient image data describing a time-dependent series of digital patient images of a target region, wherein the target region is included in an anatomical body part of a patient;

determine, based on the medical patient image data, amplitude data describing an amplitude of a vital movement of the target region;

acquire availability data describing an availability of breathing curve data describing an external breathing curve of the patient;

acquire treatment machine capability data describing imaging and beam control capabilities as well as an achievable dose rate of a plurality of radiation treatment machines;

acquire machine control data describing a treatment time associated with a size of the target region and a respective mode of different modes of imaging and beam activation by different types of treatment machines contained in the plurality of radiation treatment machines for conducting a radiation treatment and conditions for the amplitude of the vital movement, and availability of an external breathing curve associated with the size of the target region and the respective mode of the different modes of imaging and beam activation by the different types of treatment machines for conducting the radiation treatment;

determine, based on the amplitude data and the availability data and the machine control data, weight data describing individual patient-dependent weights for information contained in the machine control data and divided into a plurality of sets, wherein an individual weight is assigned to each set, of the plurality of sets, of the information;

determine, based on the amplitude data and the availability data and the machine control data and the weight data and the treatment machine capability data, machine type data describing a type of treatment machine, from the different types of treatment machines, to be used for treating the target region;

determine, based on the machine type data, treatment procedure data describing the radiation treatment to be applied to the target region using the type of treatment machine described by the machine type data;

select a treatment machine from the plurality of radiation treatment machines, based on the determined type of treatment machine and the treatment procedure data, to treat the target region; and output the treatment procedure data to the selected treatment machine to control radiation treatment parameters to reduce radiation exposure.

13. A medical system, comprising:

at least one computer comprising at least one processor and associated memory, the memory having instructions stored thereon which when executed cause the at least one processor to:

acquire medical patient image data describing a time-dependent series of digital patient images of a target region that is subject to a vital movement, wherein the target region is included in an anatomical body part of a patient;

determine, based on the medical patient image data, amplitude data describing an amplitude of the vital movement of the target region;

acquire availability data describing an availability of breathing curve data describing an external breathing curve of the patient;

acquire treatment machine capability data describing imaging and beam control capabilities as well as an achievable dose rate of a plurality of radiation treatment machines;

acquire machine control data describing a treatment time associated with a size of the target region and a respective mode of different modes of imaging and beam activation by different types of treatment machines contained in the plurality of radiation treatment machines for conducting a radiation treatment and conditions for the amplitude of the vital movement, and availability of an external breathing curve associated with the size of the target region and the respective mode of the different modes of imaging and beam activation by the different types of treatment machines for conducting the radiation treatment;

determine, based on the amplitude data and the availability data and the machine control data, weight data describing individual patient-dependent weights for information contained in the machine control data and divided into a plurality of sets, wherein an individual weight is assigned to each set, of the plurality of sets, of the information;

determine, based on the amplitude data and the availability data and the machine control data and the weight data and the treatment machine capability data, machine type data describing a type of treatment machine, from the different types of treatment machines, to be used for treating the target region;

determine, based on the machine type data, treatment procedure data describing the radiation treatment to be applied to the target region using the type of treatment machine described by the machine type data;

select, based on the determined type of treatment machine and the treatment procedure data, a treatment machine out of the plurality of radiation treatment machines to treat the target region; and output the treatment procedure data to the selected treatment machine to control parameters to reduce radiation exposure; and at least one electronic data storage device storing at least the medical patient image data and the treatment procedure data and the availability data and the treatment time data and the treatment machine capability data and the machine control data;

wherein the at least one computer is operably coupled to the at least one electronic data storage device for acquiring, from the at least one electronic data storage device, at least the medical patient image data and the availability data and the treatment machine capability data and the machine control data, and the at least one electronic data storage device for storing, in the at least one electronic data storage device, at least the treatment procedure data.

* * * * *